(12) United States Patent
Sweitzer et al.

(10) Patent No.: US 8,457,704 B2
(45) Date of Patent: *Jun. 4, 2013

(54) SINGLE USE PULSE OXIMETER

(75) Inventors: Robert Sweitzer, Milwaukee, WI (US); Guy Smith, Waukesha, WI (US)

(73) Assignee: Smiths Medical ASD, Inc., Rockland, MA (US)

( * ) Notice: Subject to any disclaimer, the term of this patent is extended or adjusted under 35 U.S.C. 154(b) by 1169 days.

This patent is subject to a terminal disclaimer.

(21) Appl. No.: 12/320,344

(22) Filed: Jan. 23, 2009

(65) Prior Publication Data

US 2009/0131774 A1    May 21, 2009

Related U.S. Application Data

(63) Continuation of application No. 11/259,093, filed on Oct. 27, 2005, now Pat. No. 7,499,739.

(51) Int. Cl.
*A61B 5/1455* (2006.01)

(52) U.S. Cl.
USPC ............................ 600/323; 600/324; 600/344

(58) Field of Classification Search
USPC ........... 600/310, 322, 323, 324, 344; 128/903
See application file for complete search history.

(56) References Cited

U.S. PATENT DOCUMENTS

| | | |
|---|---|---|
| 5,090,410 A | 2/1992 | Saper et al. |
| 5,392,777 A | 2/1995 | Swedlow et al. |

(Continued)

FOREIGN PATENT DOCUMENTS

| | | |
|---|---|---|
| JP | 2001-501847 | 2/2001 |
| JP | 2003-275183 | 9/2003 |

(Continued)

OTHER PUBLICATIONS

Dissertation thesis for an MBA class given by the inventor on Dec. 18, 2004 (not prior art). "Reducing Health Care Costs and Improving Patient Care with the Uni-Ox Pulse Oximeter from Snap Medical Technologies", Robert Sweitzer and Samatha Goetz.

(Continued)

*Primary Examiner* — Eric Winakur
(74) *Attorney, Agent, or Firm* — Louis Woo

(57) ABSTRACT

A single use, self-contained, self-powered disposable oximeter, in the form of a patch or a bandage strip, has mounted thereto a light emitter and a light sensor that together measure at least the SpO2 of the patient. Mounted to an electronics layer of the patch is an application specific integrated circuit (ASIC) that has electronics integrated thereto that controls the operation of the light emitter and light sensor, and the algorithm for calculating from the data collected by the sensor at least the SpO2 of the patient. Optionally, a display and an alarm may also be mounted or embedded onto the patch for respectively displaying at least the SpO2, and for informing the caregiver/patient that at least the SpO2 is not within an acceptable range, if such is the case. Also provided in the patch is a battery that powers the operation of the ASIC circuit and the emitter, as well as the display and alarm if such optional components are provided on the patch. An attachment mechanism is also provided on the patch. Such mechanism may be in the form of an adhesive layer that can removably attach the patch to the patient in either a transmissive mode or a reflective mode. The patch oximeter may also be equipped with a transceiver, and the appropriate electronics, for wirelessly transceiving information to/from a remote device or another wireless patch oximeter. In place of a self-contained power source, the power for operating a wireless patch oximeter may be retrieved from a remote power source, provided that the patch oximeter is within a given distance from such remote power source.

20 Claims, 15 Drawing Sheets

U.S. PATENT DOCUMENTS

| | | | |
|---|---|---|---|
| 5,490,523 A | 2/1996 | Isaacson et al. | |
| 5,511,553 A | 4/1996 | Segalowitz | |
| 5,673,692 A | 10/1997 | Schulze et al. | |
| 5,687,717 A | 11/1997 | Halpern et al. | |
| 5,746,697 A | 5/1998 | Swedlow et al. | |
| 5,823,950 A | 10/1998 | Diab et al. | |
| 5,830,137 A | 11/1998 | Scharf | |
| 5,957,854 A | 9/1999 | Besson et al. | |
| 6,011,985 A | 1/2000 | Athan et al. | |
| 6,018,673 A | 1/2000 | Chin et al. | |
| 6,154,667 A | 11/2000 | Miura et al. | |
| 6,178,343 B1 | 1/2001 | Bindszus et al. | |
| 6,215,403 B1 | 4/2001 | Chan et al. | |
| 6,374,129 B1 | 4/2002 | Chin et al. | |
| 6,387,039 B1 | 5/2002 | Moses | |
| 6,470,893 B1 * | 10/2002 | Boesen | 128/903 |
| 6,612,984 B1 | 9/2003 | Kerr, II | |
| 6,720,734 B2 | 4/2004 | Norris | |
| 6,731,962 B1 | 5/2004 | Katarow et al. | |
| 6,735,459 B2 | 5/2004 | Parker | |
| 6,845,256 B2 | 1/2005 | Chin et al. | |
| 6,942,616 B2 | 9/2005 | Kerr, II | |
| 2002/0107436 A1 | 8/2002 | Barton | |
| 2003/0009092 A1 | 1/2003 | Parker | |
| 2003/0033102 A1 | 2/2003 | Dietiker | |
| 2003/0181798 A1 * | 9/2003 | Al-Ali | 600/324 |
| 2003/0181817 A1 | 9/2003 | Mori | |
| 2004/0000713 A1 | 1/2004 | Yamashita et al. | |
| 2004/0087845 A1 | 5/2004 | Katarow | |
| 2004/0097797 A1 | 5/2004 | Porges | |
| 2004/0102687 A1 | 5/2004 | Brashears et al. | |
| 2004/0127775 A1 | 7/2004 | Miyazaki et al. | |
| 2004/0242976 A1 | 12/2004 | Abreu | |
| 2004/0260161 A1 | 12/2004 | Melker et al. | |
| 2005/0010087 A1 | 1/2005 | Banet et al. | |
| 2005/0038326 A1 | 2/2005 | Mathur | |
| 2005/0070773 A1 | 3/2005 | Chin et al. | |
| 2005/0070775 A1 | 3/2005 | Chin et al. | |
| 2005/0106713 A1 | 5/2005 | Phan et al. | |
| 2005/0113655 A1 | 5/2005 | Hull | |
| 2005/0119580 A1 | 6/2005 | Eveland | |
| 2005/0131288 A1 | 6/2005 | Turner et al. | |
| 2005/0197550 A1 | 9/2005 | Al-Ali et al. | |
| 2005/0228298 A1 | 10/2005 | Banet et al. | |
| 2005/0228299 A1 | 10/2005 | Banet | |
| 2005/0234317 A1 | 10/2005 | Kiani | |
| 2005/0245839 A1 | 11/2005 | Stivoric | |

FOREIGN PATENT DOCUMENTS

| | | |
|---|---|---|
| JP | 2004-24551 | 1/2004 |
| RU | 2199723 | 6/1996 |
| WO | 98/15224 | 4/1998 |
| WO | 0141634 | 6/2001 |
| WO | 2005/092177 | 10/2005 |

OTHER PUBLICATIONS

"An Integrated Pulse Oximeter System for Telemedicine Applications", Crilly et al., IEEE Instrumentation and Measurement Technology Conference, Ottawa, Canada, May 19-21, 1997.

"Medicine" Textbook of Anaesthesiology/Ed. By Aitkenhead A.R. et al., vol. 1, 1999, pp. 437-440 (English translation)attached).

* cited by examiner

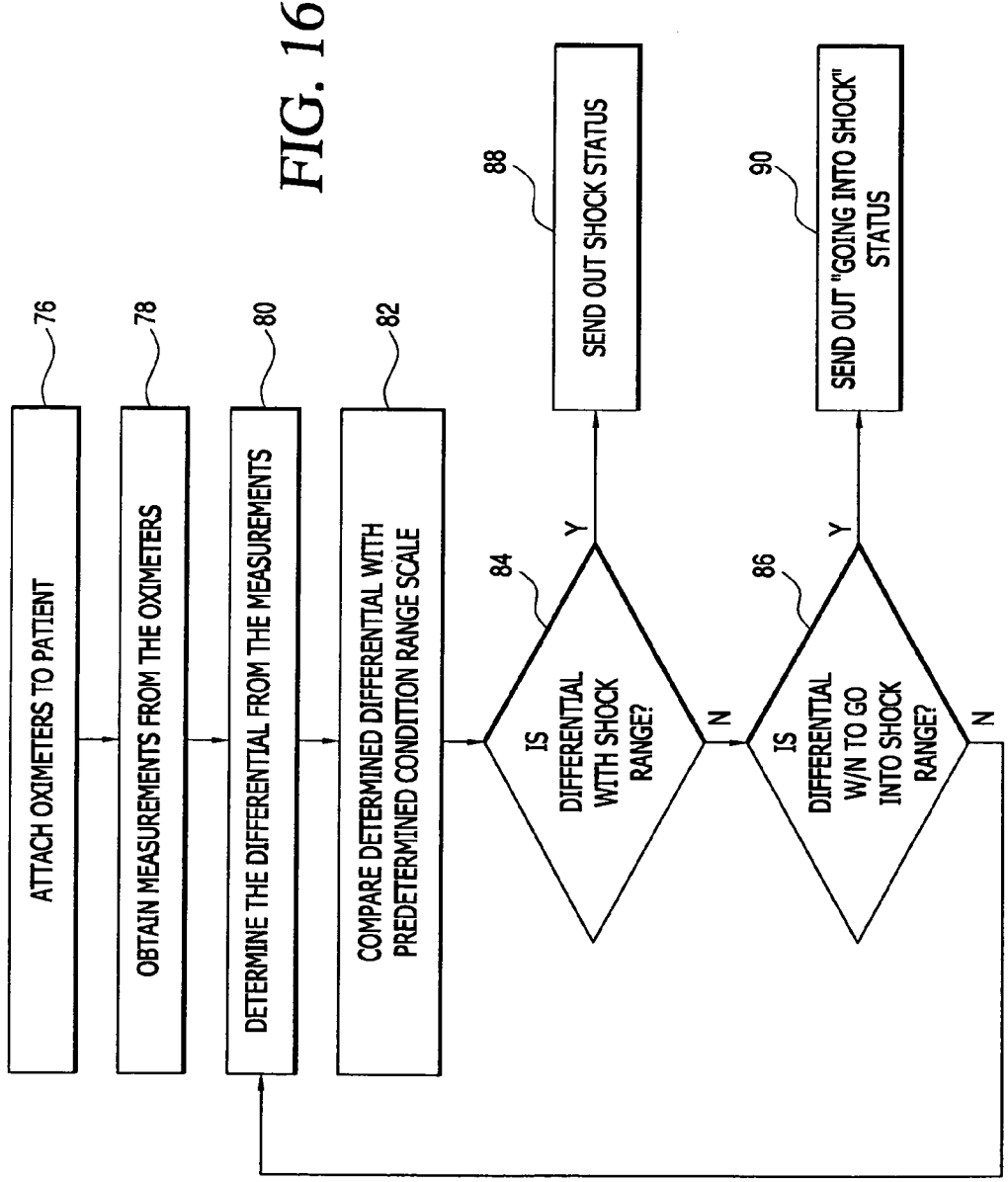

SINGLE USE PULSE OXIMETER

CROSS REFERENCES TO RELATED APPLICATIONS

The instant application is a continuation of application No. 11/259,093 filed Oct. 27, 2005, now U.S. Pat. No. 7,499,739.

FIELD OF THE INVENTION

The present invention relates to oximeters and more particularly to a single use oximeter that is self-contained in a patch, such as for example a self-adhesive bandage. The present invention further relates to a disposable patch oximeter having telecommunication capabilities.

BACKGROUND OF THE INVENTION

Oximeters are well known. Prior to the instant invention, self-contained oximeters come in the form of bulky housings that clip onto the finger of a patient, such as that disclosed in U.S. Pat. No. 5,792,052. Another example of a self-contained oximeter is that disclosed in U.S. Pat. No. 6,654,621, assigned to the assignee of the instant application. In these prior art self-contained finger oximeters, electronics are contained in housings that pivotally grasp the finger of a patient ('052 patent) or a housing that forms an opening to which the finger of the patient is inserted ('621 patent). Once the oxygen saturation level of the patient is determined, these finger oximeters may be removed from the patient and used on other patients, as these finger oximeters are reusable devices.

There is also in the market a bandage that has embedded therein the light emitter and sensor of an oximeter. The electronics for operating the light emitter and sensor and to which the bandage is connected is located remotely from the bandage. This device is disclosed in U.S. Pat. Nos. 6,735,459, 6,721,585, 6,684,091, 6,519,487, 6,343,224, 6,321,100 and 6,144,868. Only the bandage is disposable in this device.

SUMMARY OF THE PRESENT INVENTION

The present invention is a self-contained, fully disposable, single use pulse oximeter that activates when the backing paper for its adhesive is peeled off. All of the components for the oximeter are mounted, integrated, or embedded to a multi-layered patch, or bandage. In addition to the light or radiation emitter that outputs a multifrequency light to the patient, be it the digit or the forehead of the patient, and the sensor or detector that senses the light passing through, or reflecting from, the patient for obtaining data from the patient and then calculating the oxygen saturation level of blood (SpO2) from the acquired data, the other components for the pulse oximeter are also mounted to the patch. This includes the oximetry circuitry, an optional display, an optional alarm possibly in the form of a piezoelectric transducer (audible) and/or an optical indicator on the display (visual) and the power source. The circuitry may be integrated to an application specific integrated circuit (ASIC) platform or chip, and is embedded to a layer of the bandage that is protected by at least two thin barrier layers that are immune to moisture and prevent the ASIC from being exposed to the environment. The power source may be a thin conventional button battery, or a fuel cell battery, that may also be embedded in the same layer as the ASIC chip. The same layer of the bandage may also include the optional display and alarm. Alternatively, the display and the alarm may be formed at a layer of the bandage that is above the ASIC platform layer and beneath a protective membrane layer that may include preprinted graphics. Membrane switches may also be provided under the protective membrane to provide the user the capability to activate a limited number of functions, as for example turning on/off the alarm and/or display.

The bandage is a sterile bandage with a peel off sheet covering its lower most adhesive layer that allows the bandage to be removably attached to the patient. To provide additional sterility, the bandage may be stored or housed in a sterile package that may have a removable cover.

The light emitter and detector are positioned onto the patch depending on whether the patch is to be used in a transmissive mode in which the patch, or bandage, is wrapped around a digit or an earlobe of a patient, or in a reflective mode whereby the patch is adhesively secured to the forehead, or another substantially flat surface, of the patient.

Telecommunication capabilities may also be added to the disposable patch oximeter of the instant invention. For the wireless patch oximeter, a transmitter or transceiver is mounted to, or embedded in, the patch or bandage. The circuitry required for transmitting or transceiving the signals to/from the patch oximeter are either added or integrated to the ASIC chip, or is added as a separate circuit to the electronics layer of the patch.

For the patch oximeter of the instant invention, be it the stand alone bandage or the wireless bandage, the most convenient way in which to attach the bandage to the patient is by means of an adhesive layer, as is conventionally done in conventional bandages that are used to cover cuts on an individual. However, other attachment mechanisms may also be used for the instant invention patch oximeter or bandage. Such attachment mechanisms may include for example velcro or snaps that would allow the bandage to be securely attached to the patient. Instead of a full layer of adhesive, only portions of the lower most layer of the bandage need to be provided with the adhesive in order to enable the bandage to be removably attachable to a patient.

With respect to the wireless version of the inventive patch oximeter, in addition to being able to wirelessly communicate with a host monitor system where at least the patient's oxygen saturation level of arterial blood (SpO2) is remotely monitored, each patch oximeter may also be able to communicate with another similar patch oximeter that is attached to another location on the patient. With at least two oximeters attached to the patient, a differential of the SpO2 of the patient may be obtained, so that a hypovolemic shock determination could be made on the patient, i.e., whether the patient is just bleeding, on the verge of going into shock, or in fact is in shock.

Electrodes may also be added to the bandage oximeter of the instant invention, so that physiological parameters other than the oxygen saturation level of the arterial blood of the patient, for example EEG, ECG, EKG, etc., may be obtained from the patient, at the same time that the SpO2 is being obtained from the patient. For measuring additional physiological parameters from the patient, additional electronics that enable the patch oximeter to perform additional measurement functions are either integrated to the ASIC circuit, or mounted to the electronics layer of the patch as separate additional circuits.

With respect to the wireless patch oximeter, instead of embedding the power source onto the patch, a power source remote from the patch, which would supply power to the patch when the patch comes within a predetermined or given distance from the remote power source, may be used. For this radio frequency identification (RFId) equipped embodiment, an antenna coil, as well as an RF power receiver, are added to the oximeter patch, so that power may be retrieved from the remote power source when the bandage comes within communication distance from the remote power source. For this embodiment, and possibly other wireless embodiments of the inventive patch oximeter, the display and/or the alarm may not be needed on the patch.

The present invention is therefore a one-piece disposable flexible patch or bandage adaptable to be attachable to a patient for measuring at least the oxygen saturation level of arterial blood of the patient. This disposable patch has mounted thereto a light emitter and a light detector to detect the light from the light emitter that passes through the patient so that data relating to at least the SpO2 of the patient is acquired. Also mounted to the disposable patch is an electronic circuit for effecting operation of the light emitter and the light detector, and to calculate from the data acquired at least the SpO2 of the patient. An attachment mechanism is also provided at the patch to enable the patch to be removably attached to the patient.

The present invention also relates to an oximeter that comprises a patch that is adapted to be attached to the patient. The oximeter includes a light emitter and a light detector each mounted to the patch, with the light detector detecting the light from the light emitter that passes through the patient. An electronic circuit also mounted to the patch operates the light emitter and the light detector, and calculates from the data acquired by the light detector at least the oxygen saturation level of arterial blood of the patient. Means is provided at the patch to enable the patch to be removably attached to the patient.

The instant invention further relates to a method of making a disposable oximeter that includes the steps of: a) obtaining a flexible patch adaptable to be attached to a patient; b) mounting a light emitter and a light detector to the patch; c) ensuring that the light detector and the light emitter are arranged on the patch to work cooperatively with each other so that the light detector would detect the light from the light emitter that passes through the patient, or reflected back from the patient, and acquires data relating to at least the oxygen saturation level of arterial blood of the patient; d) mounting an electronic circuit to the patch for effecting operation of the light emitter and the light detector, and to calculate from the acquired data at least the oxygen saturation level of arterial blood of the patient; and e) providing means to the patch to enable the patch to be removably attached to the patient.

The wireless one-piece disposable oximeter of the instant invention is a one-piece disposable patch that is adapted to be attached to a patient for measuring at the oxygen saturation level of arterial blood of the patient. The wireless patch oximeter includes a light emitter mounted to the patch, a light detector mounted to the patch to detect the light from the light emitter that passes through the patient, or reflected back from the patient, so that data relating to at least the oxygen saturation level of the arterial blood of the patient may be acquired, an electronic circuit mounted to the patch for effecting operation of the light emitter and the light detector, and to calculate from the data acquired the oxygen saturation level of arterial blood of the patient, a transceiver mounted to the patch to at least transmit the calculated oxygen saturation level of arterial blood or data acquired of the patient to a remote device, and an attachment mechanism at the patch that enables the patch to be removably attached to the patient.

The oximeter of the instant invention furthermore includes a patch adaptable to be attached to the patient, a light emitter and a light detector each mounted to the patch, an electronic circuit mounted to the patch for effecting operation of the light emitter and the light detector, and to calculate from the data acquired by the light detector due to the light from the light emitter that passes the patient it senses, at least the oxygen saturation level of the arterial blood of the patient, a transceiver mounted to the patch to enable the patch to at least transmit the signal representing the oxygen saturation level of arterial blood of the patient or the data acquired by the light detector to a remote device, and means provided at the patch to enable the patch to be removably attached to the patient.

The present invention also relates to a method of determining whether a patient is in hypovolemic shock that includes the steps of: a) attaching at least two oximeters to different areas of the patient, with each of the oximeters being a patch adaptable to be attached to the patient. Each of the patch oximeters has mounted thereto a light emitter, a light detector, an electronic circuit for operating the light emitter and light detector and to calculate from the data acquired by the light detector of light from the light emitter that passes through the patient at least the oxygen saturation level of arterial blood of the patient, a transceiver that allows the patch to communicate the calculated oxygen saturation level of arterial blood of the patient to a remote device or to another oximeter attached to the patient, and means that enables the patch to be removably attached to the patient; b) determining the difference between the respective oxygen saturation levels of blood of a patient measured by each of the oximeters attached to the patient; and c) comparing the determined difference with a predetermined condition to decide whether the patient is in shock.

BRIEF DESCRIPTION OF THE FIGURES

The instant invention will become apparent and will best be understood by reference to the following description of the invention taken in conjunction with the accompanying drawings, wherein:

FIG. 16 is a flow diagram illustrating the processes of determining whether the patient shown in FIG. 15 is in shock.

DETAILED DESCRIPTION OF THE INVENTION

Figure 1:
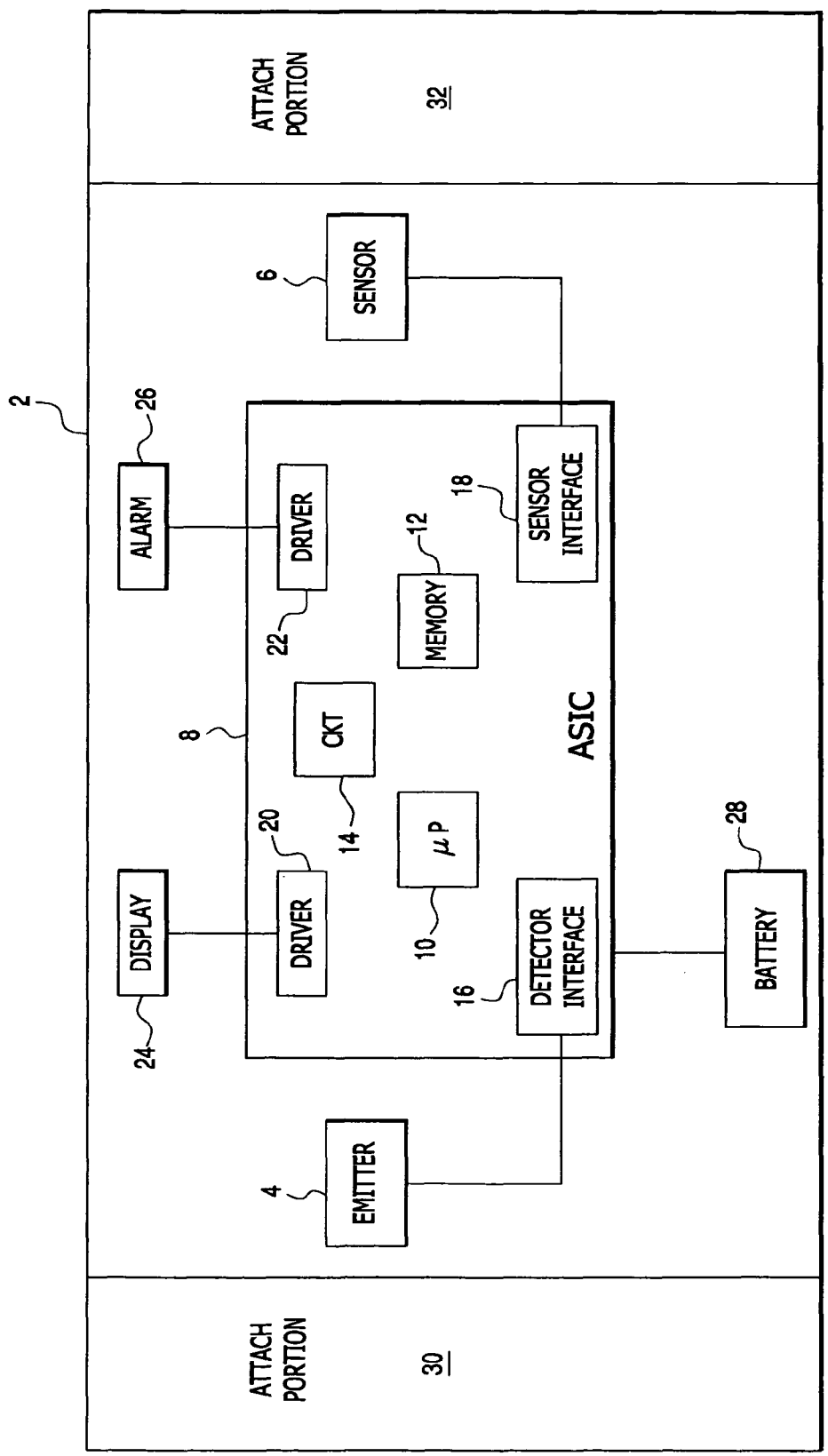
FIG. 1 is a block diagram of the oximeter patch or bandage of the instant invention, with the light emitter and the light detector being positioned on the patch to operate in a transmissive mode to measure the oxygen saturation level of arterial blood of the patient when the patch is wrapped around a digit or an earlobe of the patient.

With reference to FIG. 1, a flexible patch 2, in the form of a bandage or strip, has mounted thereto a light or radiation emitter 4 and a photodetector or sensor 6. As is well known, light emitter 4 may be made up of a number of LEDs each outputting a light at a different frequency, so that emitter 4 in essence outputs a multifrequency light to a part of the patient, be that part a digit, the bridge of the nose, an earlobe, the forehead or some other body part of the patient. Photodetector 6 then senses or detects the light that passes through the patient as data obtained from the patient.

Also mounted onto patch 2 is an application specific integrated circuit (ASIC) 8, possibly in the form of a flexible circuit platform or chip, in which the various electronic components for controlling emitter 4 and sensor 6, as well as for calculating from the data collected or acquired by sensor 6 at least the oxygen saturation level of arterial blood (SpO2) and the heart rate of the patient. As shown in FIG. 1, in accordance with the conventional processes for manufacturing an ASIC chip, representative electronic components required for the operation of a pulse oximeter are formed or integrated into the ASIC circuit 8. These include a processor 10, a memory 12, an electronic circuit 14 specifically designed for performing the oximetry functions, an emitter or detector interface circuit 16, a sensor interface circuit 18, a display driver 20 and an alarm driver 22. Other electronics that may also be integrated to the ASIC circuit 8 are not shown for the sake of simplicity. For the oximeter embodiments discussed herein, ASIC circuit 8 is presumed to be in the form of a thin chip that may be flexible and/or is mounted or embedded in a particular layer of the patch, as will be discussed in more detail, infra.

The algorithm for performing the SpO2 analysis may be that described in U.S. Pat. No. 5,558,096, assigned to the assignee of the instant invention. The disclosure of the '096 patent is incorporated by reference herein. Other algorithms or software that may be needed for effecting the operation of emitter 4 and sensor 6 in a conventional way may also be stored in memory 12. Moreover, the software for operating other components or electronics that are to be discussed hereinbelow may also be stored in memory 12.

For the oximeter shown in FIG. 1, also mounted to the patch 2 is a display 24, an alarm 26, and a power source in the form of a battery 28. Display 24 may be a thin membrane LCD display while alarm 26 may be a piezoelectric transducer that conceivably could be integrated as a separate electronic component mounted on patch 2. Battery 28, for the instant invention oximeter, may be a conventional thin plate battery or a fuel cell battery that self activates when the patch is removed from its sterile packaging. A chemical light source that also self activates when the patch is removed from its sterile package, or having its adhesive backing strip removed, may be used as an illumination source for display 24. Using a chemical illumination source would extend the battery life. Self activation would eliminate the need for an "on" switch. Further, the illumination source could be automated to sense ambient lighting conditions to determine the need for the illumination source, thereby conserving battery power when self-illumination is not required. For the instant invention, the duration of the chemical light may be adjusted to mirror the life of the battery.

For illustration purposes, also provided at patch 2 are attached portions 30 and 32. Even though shown as separate portions, it should be noted that such attached portions may in fact be an adhesive layer at the face of the patch that comes into contact with the patient for adhesively attaching the patch to the patient. Attach portions 30 and 32 may also be made of velcro, so that the patch, in the form a bandage, may be wrapped around a digit or an earlobe of the patient. Other types of attach mechanisms such as clasps or snaps may also be used. This is particularly true insofar as emitter 4 and sensor 6, as shown in the FIG. 1 embodiment, are arranged or oriented to work cooperatively in a transmissive mode when the patch oximeter is wrapped around the digit, earlobe or bridge of the nose of the patient. A more detailed discussion of the various layers of the oximeter patch will be given below with respect to the discussion of FIG. 12.

Figure 2:
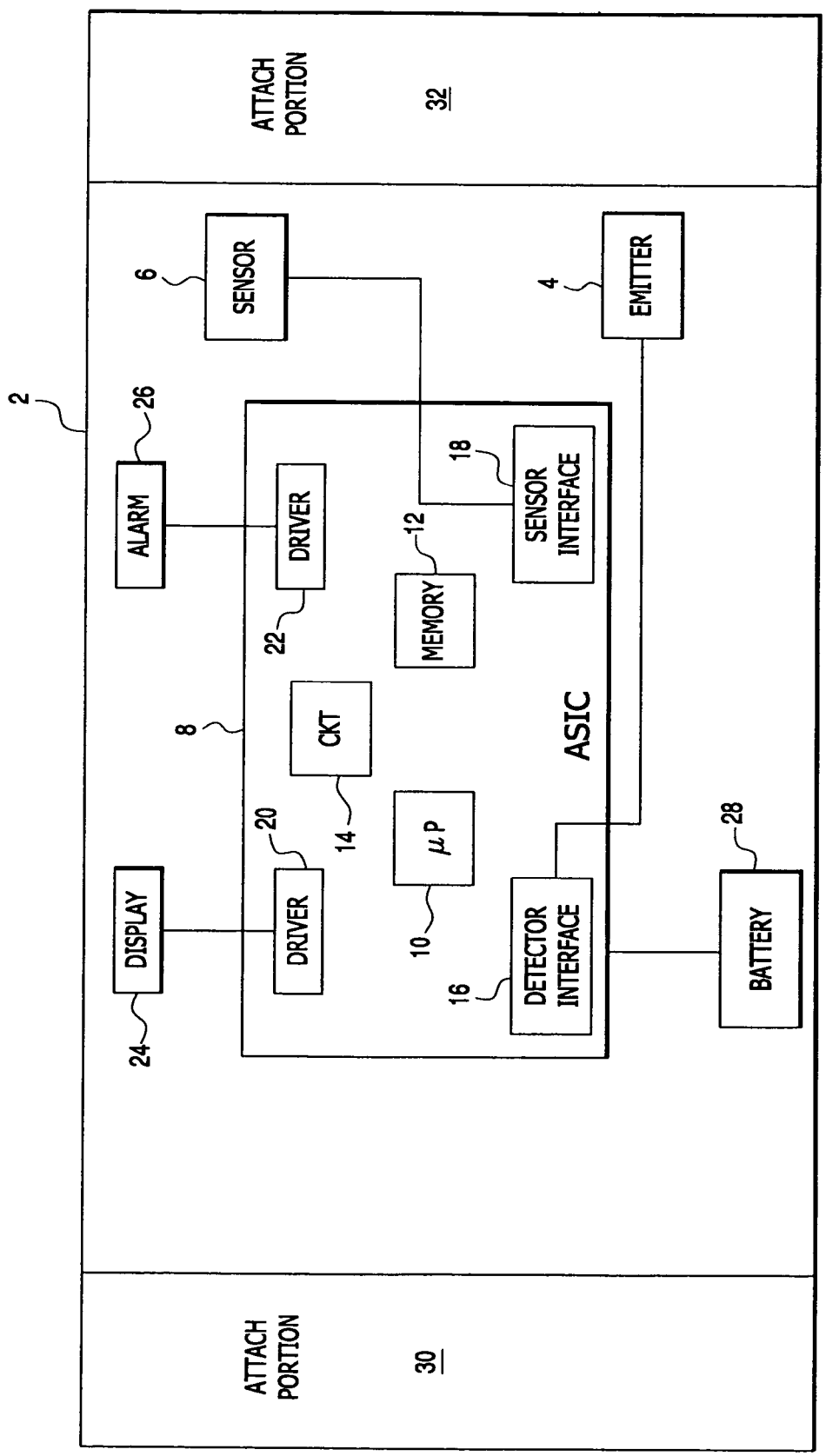
FIG. 2 is a block diagram of the patch oximeter of the instant invention in which the orientation of the light detector and light emitter as mounted to the patch is such that the oximeter is adaptable to operate in a reflective mode, with the patch being adhesively attached to the forehead, or another substantially flat surface, of the patient.

FIG. 2 has the same components as those shown in FIG. 1. The same components in FIG. 2, as well as those same components in the other figures to be discussed, are accordingly labeled the same. The one difference between the patch oximeter shown in FIG. 2 from that shown in FIG. 1 is the placement of the emitter 4 and sensor 6 on the patch. As shown, emitter 4 and sensor 6 are mounted in defined proximity to each other on the patch, so as to enable the patch oximeter to measure the SpO2 of the patient reflectively. Thus, the reflective mode patch oximeter of FIG. 2 is best adapted to attach to the forehead, or another substantially flat skin surface, of the patient.

Figure 3:
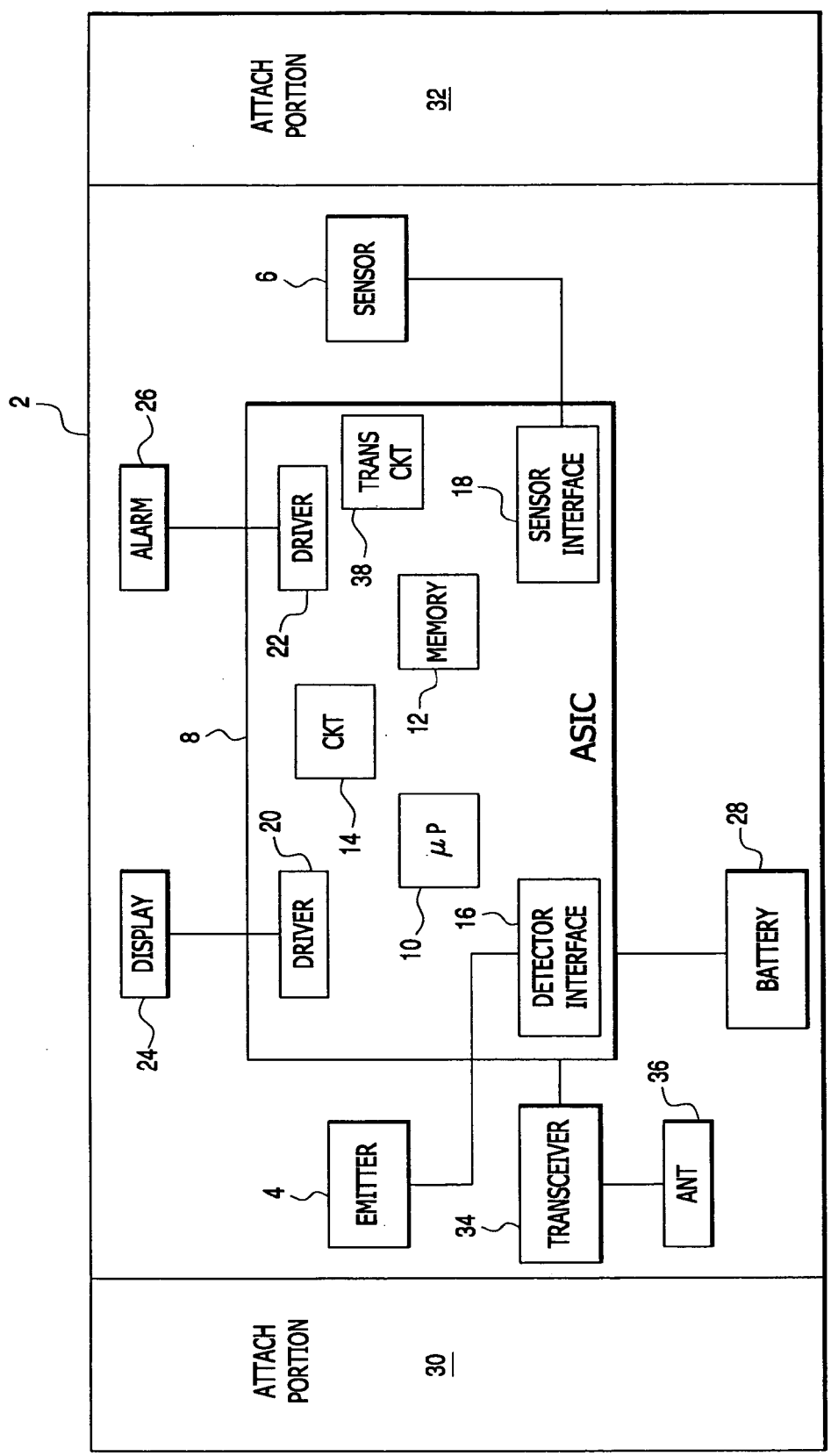
FIG. 3 is a block diagram of the patch oximeter of the instant invention in which a transmitter or transceiver, and appropriate electronics for operating the same, are added to the patch to enable the patch oximeter to wirelessly communicate with a remote device.

FIG. 3 shows another embodiment of the instant invention in which, in addition to having all of the components of the previously discussed embodiments, the patch oximeter further has electronic components mounted thereto that enable it to operate as a wireless patch oximeter. In particular, a transmitter or transceiver 34 is added to the electronics layer of the patch, and an antenna 36 coupled to transceiver 34 provides the means by which signals may be transmitted and/or transceived to or from the patch oximeter. To provide additional functionalities that are required for the operation of the transceiver 34, electronics in the form of a transmission circuit 38 is added to the electronics layer of the patch, either as a separate circuit or integrated to the ASIC circuit 8. The functionalities of the transceiver 34 and its associate transmission circuit 38 may be gleaned from assignee's U.S. Pat. No. 6,731,962, the disclosure of which being incorporated by reference herein.

As the patch oximeter is equipped with a transceiver 34, not only could the patch oximeter transmit information to a remote device, it could likewise receive information from the remote device. For example the patch oximeter may ordinarily be in a sleep mode, and may be awakened by a signal from the remote device that awakens the patch oximeter to begin its monitoring or measurement. By way of another example, the last transmission of the patch oximeter may not have been correctly received by the remote device and hence the remote device could request the patch oximeter to resend the data.

Even though the light emitter 4 and sensor 6 of the wireless patch oximeter embodiment are shown to be arranged for operating in the transmissive mode, it should be appreciated that the wireless patch oximeter could likewise work in the reflective mode by simply rearranging the respective positions of emitter 4 and sensor 6 as shown per the FIG. 2 embodiment.

With the wireless functionalities, the patch oximeter of FIG. 3 is capable of at least transmitting the calculated SpO2 of the patient to a remote device, for example a monitor system such as the assignee's Vital Sign monitor equipped with the appropriate telecommunication transceiver such as for example an RF transmitter with its RF link, for displaying and/or recording the patient's SpO2 at the remote device. With transceiver 34 being integrated to the patch oximeter, the information or data acquired by sensor 6, or by the to be discussed electrodes added to the patch oximeter, may be transmitted to a similar wireless patch oximeter, so that a mini telecommunication network may be established among a plurality of wireless patch oximeters to enable the medical personnel to closely monitor the different physiological parameters of the patient. Such monitoring will be discussed in more detail, infra, with respect to FIG. 15.

Figure 4:
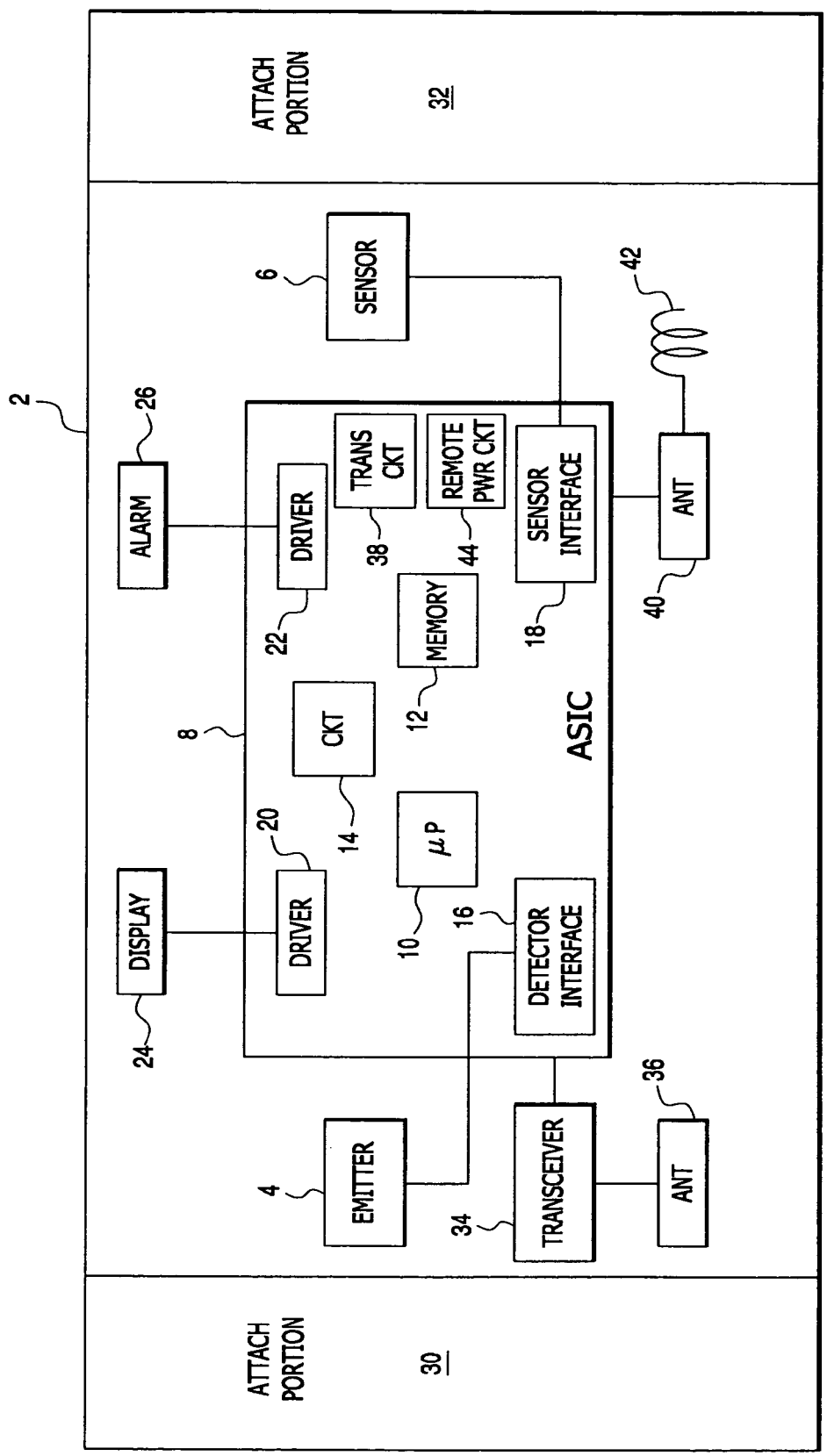
FIG. 4 is a block diagram of a wireless patch oximeter with no power source provided on the patch, but with an antenna and a coil added to the patch to retrieve and utilize power provided from a remote power source.

FIG. 4 illustrates another embodiment of the instant invention in which the battery power source has been removed from the patch oximeter. Instead, power for the patch oximeter is obtained remotely by the incorporation of an antenna 40 and a coil 42. Antenna 40 is optional, as coil 42 is the component that allows the patch oximeter to receive power from a remote power source. The electronics that may be required to provide the functionalities to retrieve power remotely is added to the patch by way of a remote power circuit 44. The operation of the remote power grab is similar to the conventional RFID (radio frequency identification) technology that is being used for identifying goods. One example of the use of such RFID technology is in the miniaturized electronic circuit labels that are placed on items, for example, that would identify the items when they are sold. If perchance the customer had not paid for an item, when the item is taken past the cash register or out the store, an alarm is triggered. The electronic circuit that operates to trigger the alarm gets its power from a remote power source. The same scenario may be used with the FIG. 4 wireless patch oximeter, with the proviso that the power required for operating the patch oximeter embodiment such as that shown in FIG. 4 be increased by at least two fold, so that a sufficient level of power is provided for the operation of emitter 4.

Figure 5:
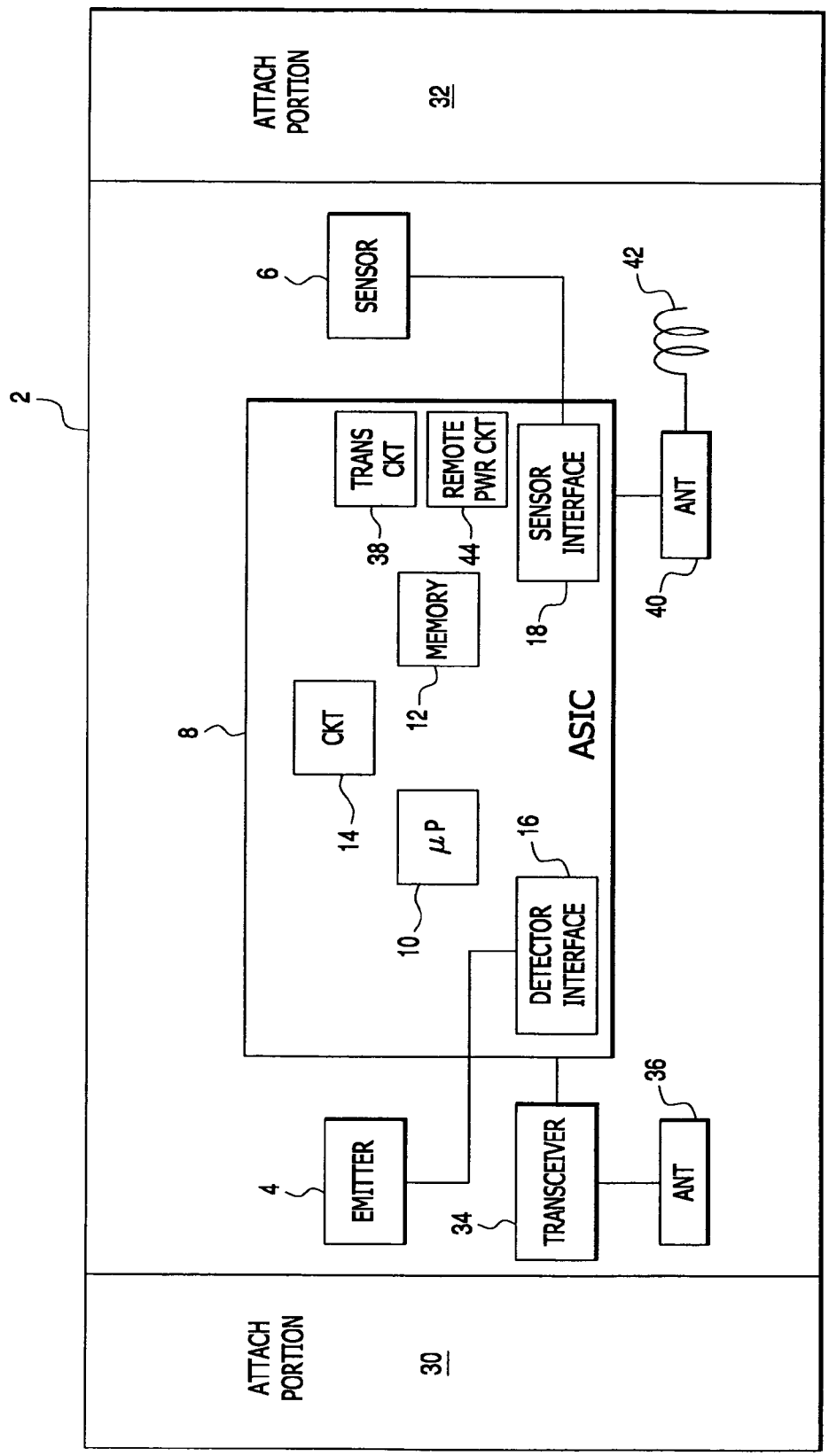
FIG. 5 is a different embodiment of the FIG. 4 wireless patch oximeter in which the display and alarm, in addition to their respective drivers, are removed from the patch.

For the FIG. 4 embodiment, even though display 24 and alarm 26 remain, it should be appreciated that those components may not necessarily be needed, especially when there is no need for the patient to look at the display, as for example when the patient wears the patch oximeter because she is in a sleep study involving for example sleep apnea, whereby the readings from the patient are displayed remotely on a remote monitor. A patch oximeter that does not include the display and alarm components, and their respective drivers, is shown in FIG. 5. As was mentioned previously, for all of the disclosed embodiments, it is assumed that the patch oximeter is adapted to work in both the transmissive mode and the reflective mode, irrespective of how the emitter 4 and sensor 6 are shown to be positioned in the figures.

Figure 6:
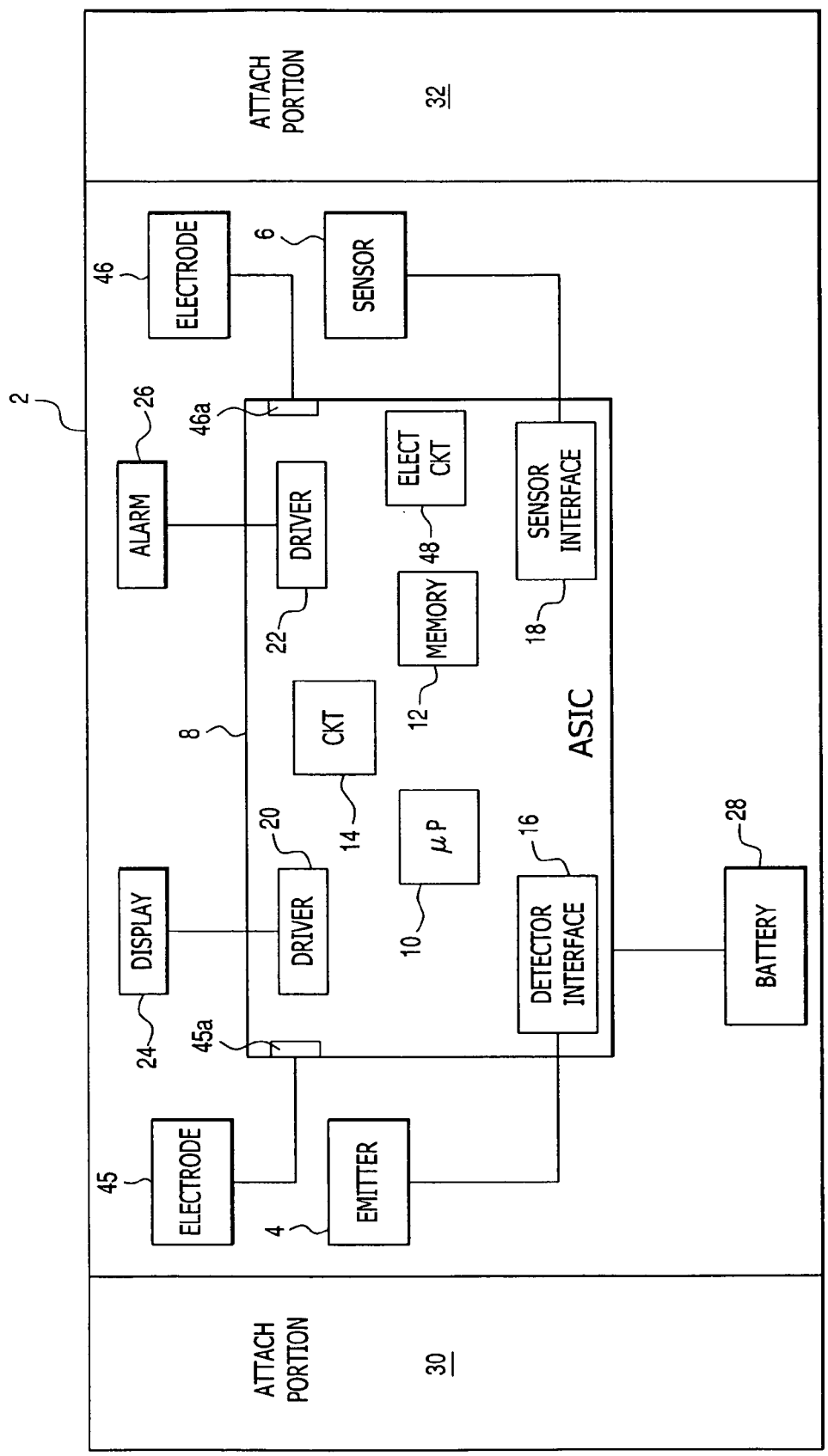
FIG. 6 is a block diagram of a patch oximeter that has at least two electrodes added to the patch to enable the patch oximeter to obtain from the patient at least one other physiological parameter in addition to the SpO2, which is obtained in a transmissive mode.

Another aspect of the instant invention is illustrated by the block diagram of the strip or bandage shown in FIG. 6. As shown, the disposable patch oximeter of FIG. 6 has added thereto two electrodes 45 and 46, and their respective interface circuits 45a and 44b, which may be integrated to the ASIC circuit 8, or as additional electronics mounted separately to the electronics layer of the patch 2. Additional electronics represented by electrode circuit 48 may also be integrated to the ASIC circuit 8, or be mounted as an individual component on the electronics layer of the patch 2. In either event, electrodes 45 and 46 are conventional bioelectric electrodes (without limitation for example silver-silver chloride, possibly pre-jelled electrodes) that, when positioned at a distance from each other (or formed concentrically), are able to measure additional physiological parameters of the patient, such as for example EKG, ECG, etc. EKG and ECG are well known physiological parameters associated with the electrical stimuli of the heart. The addition of electrodes to measure bioelectric events permits the determination of time differences between the ECG QRS complex and the patient's plethysmograph waveform which has been shown to correlate withnon-invasive blood pressure (NIBP).

In addition to the above mentioned physiological parameters that involve the pulse, the heart rate and the SpO2 of the patient, an electrode or sensor in the form of a temperature probe may also be added to the patch, along with the appropriate electronics, to measure the temperature of the patient. Thus, with the patch oximeter of FIG. 6, in addition to SpO2 and heart rate, other types of physiological parameters such as temperature, blood pressure, in the form of a non-invasive blood pressure (NIBP) could be continuously monitored, or obtained.

Figure 7:
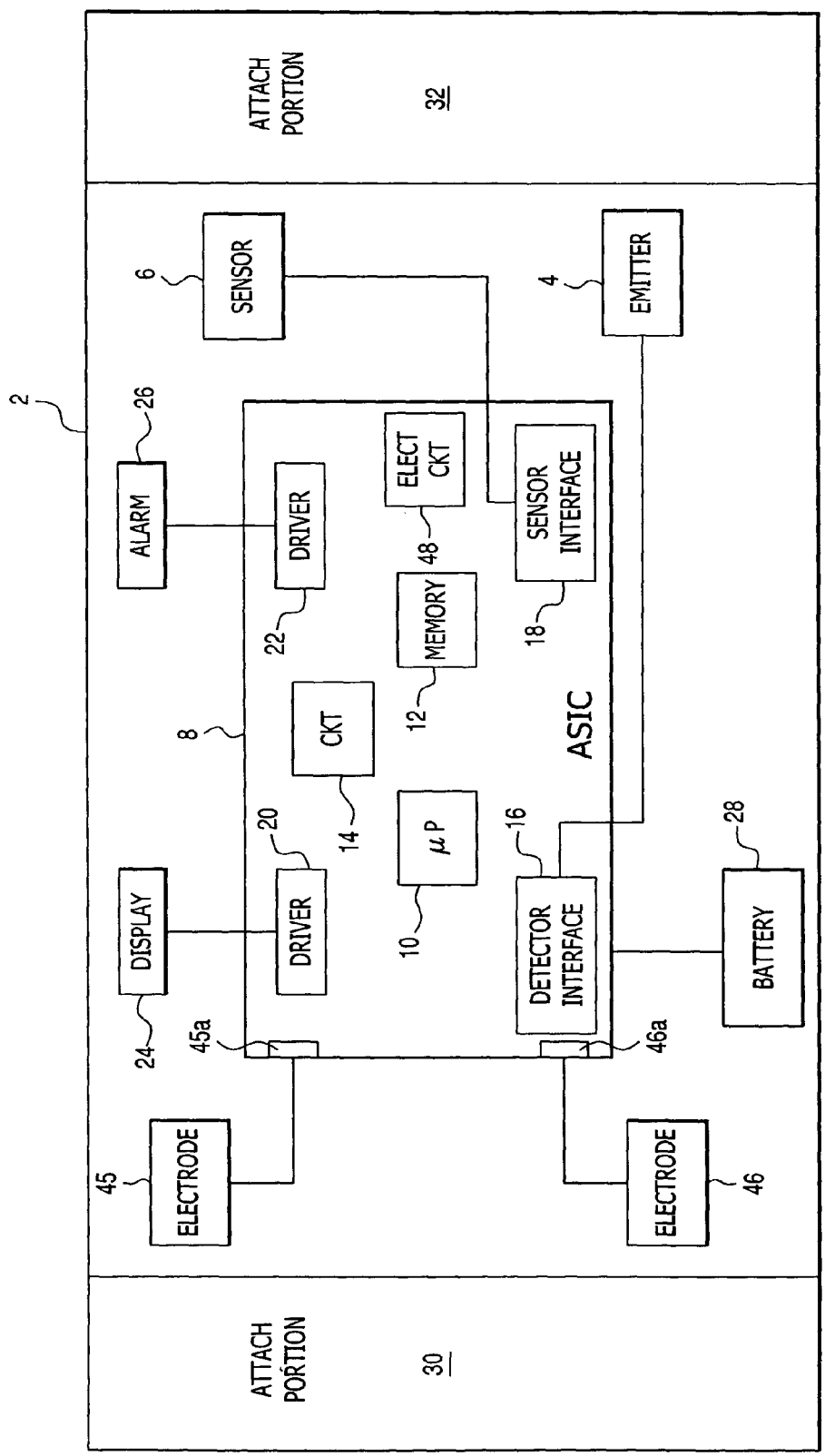
FIG. 7 is a block diagram showing a patch oximeter that is the same as that shown in FIG. 6, but with the light emitter and the light detector oriented to operate in a reflective mode.

FIG. 7 shows in block diagram format the possible different placements of electrodes 45 and 46, as well as the placement of emitter 4 and sensor 6 on the patch, in the event that the SpO2 to be obtained from the patient needs to be done on the patient's forehead, or another substantially flat surface of the patient, via the reflective mode.

Figure 8:
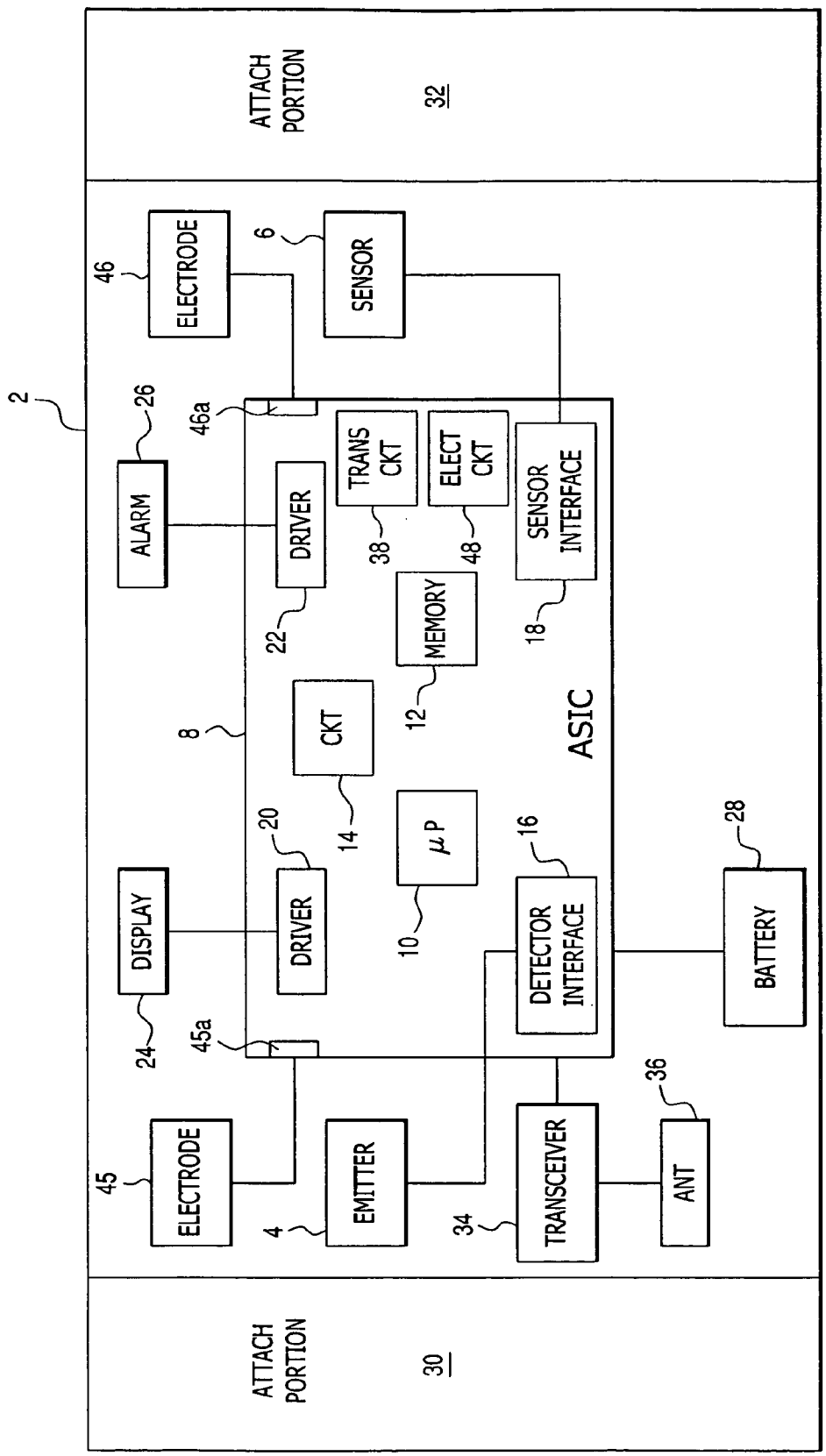
FIG. 8 is a block diagram illustrating a wireless patch oximeter configured with electrodes to obtain additional physiological parameters of the patient.

FIG. 8 shows a wireless patch oximeter with ECG electrodes 45 and 46, and the electrode circuit 48 for acquiring the data measured by the electrodes. For the FIG. 8 embodiment, in addition to the SpO2 and data collected by sensor 6 for calculating at least the SpO2, data relating to other physiological parameters of the patient, as collected by electrodes 45 and 46, may likewise be transmitted to a remote device, such as the previously mentioned Vital Signs monitor for display and/or recording. It should be appreciated that even though separate telecommunications circuit 38 and electrode circuit 48 are shown, those circuits may in fact be incorporated into the main electronic circuit 14 of the ASIC circuit 8 mounted to the electronics layer of patch 2.

Figure 9:
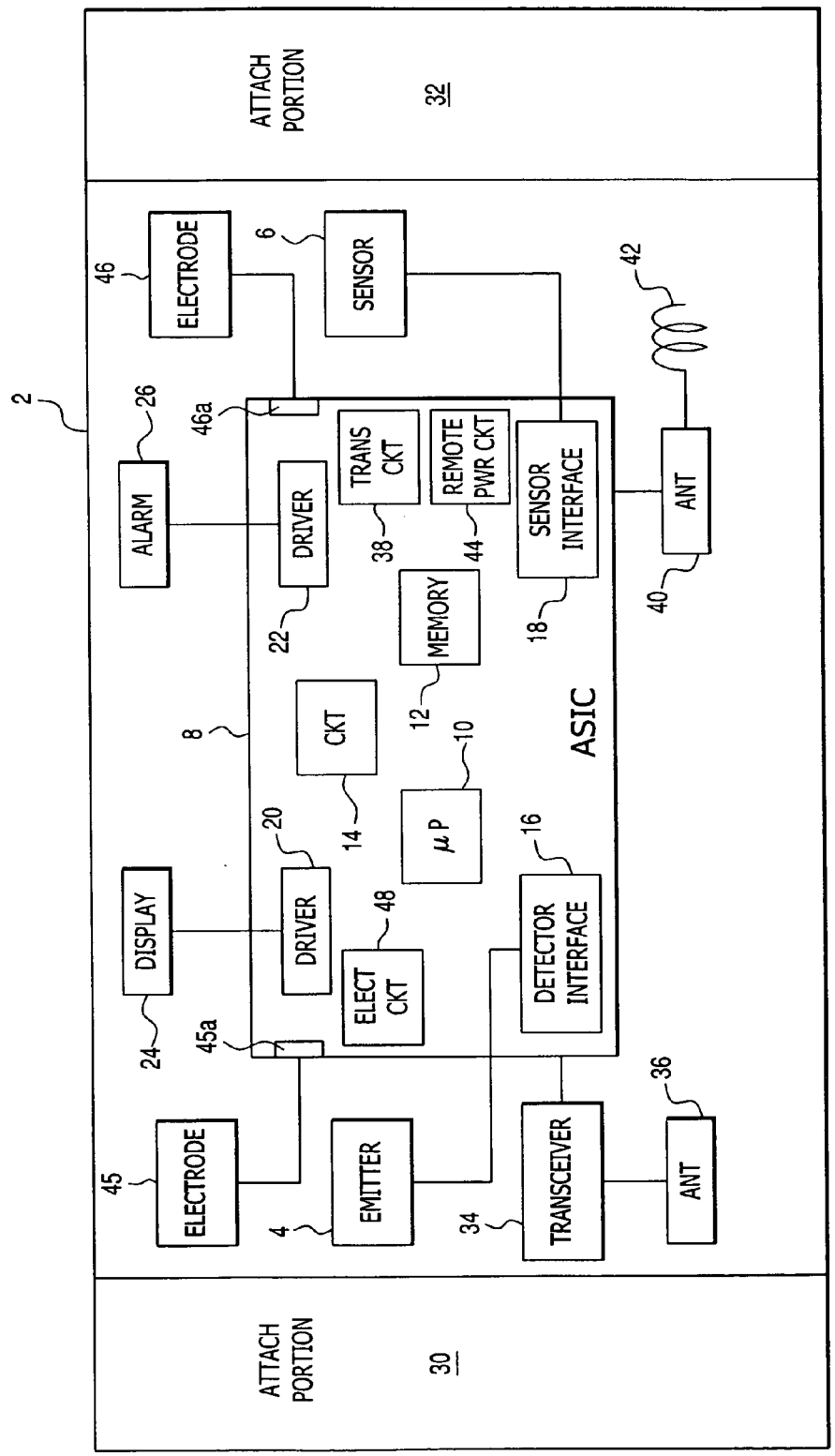
FIG. 9 is a block diagram of a wireless patch oximeter with electrodes mounted to the patch that is powered by a remote power source.

FIG. 9 illustrates in block diagram format the embodiment of the wireless patch oximeter of the instant invention where SpO2, heart rate and other physiological parameters may be measured from the patient. The FIG. 9 embodiment is similar to the FIG. 4 embodiment in that the power for the operation of the patch oximeter is retrieved from a remote power source when the patch oximeter comes within a given distance from the remote power source. Thus, for the patch oximeter of FIG. 9, as well as for the remote power access patch oximeters described in FIGS. 4 and 5, the patch oximeter attached to the patient may not be activated until the patient gets within a given distance from the remote power source, in which case the electronic circuit, for example circuit 14, would awake to activate the remaining electronic circuits to perform their respective functions, and power up emitter 4. If sufficient power is accessed from the remote power source, the patient may also be able to view, per display 24, her SpO2 and heart rate, as well as the ECG and possibly a strength bar graph. Membrane switches, not shown, may be provided on the top layer of the patch to activate/deactivate alarm 26, and/or display 24.

Figure 10:
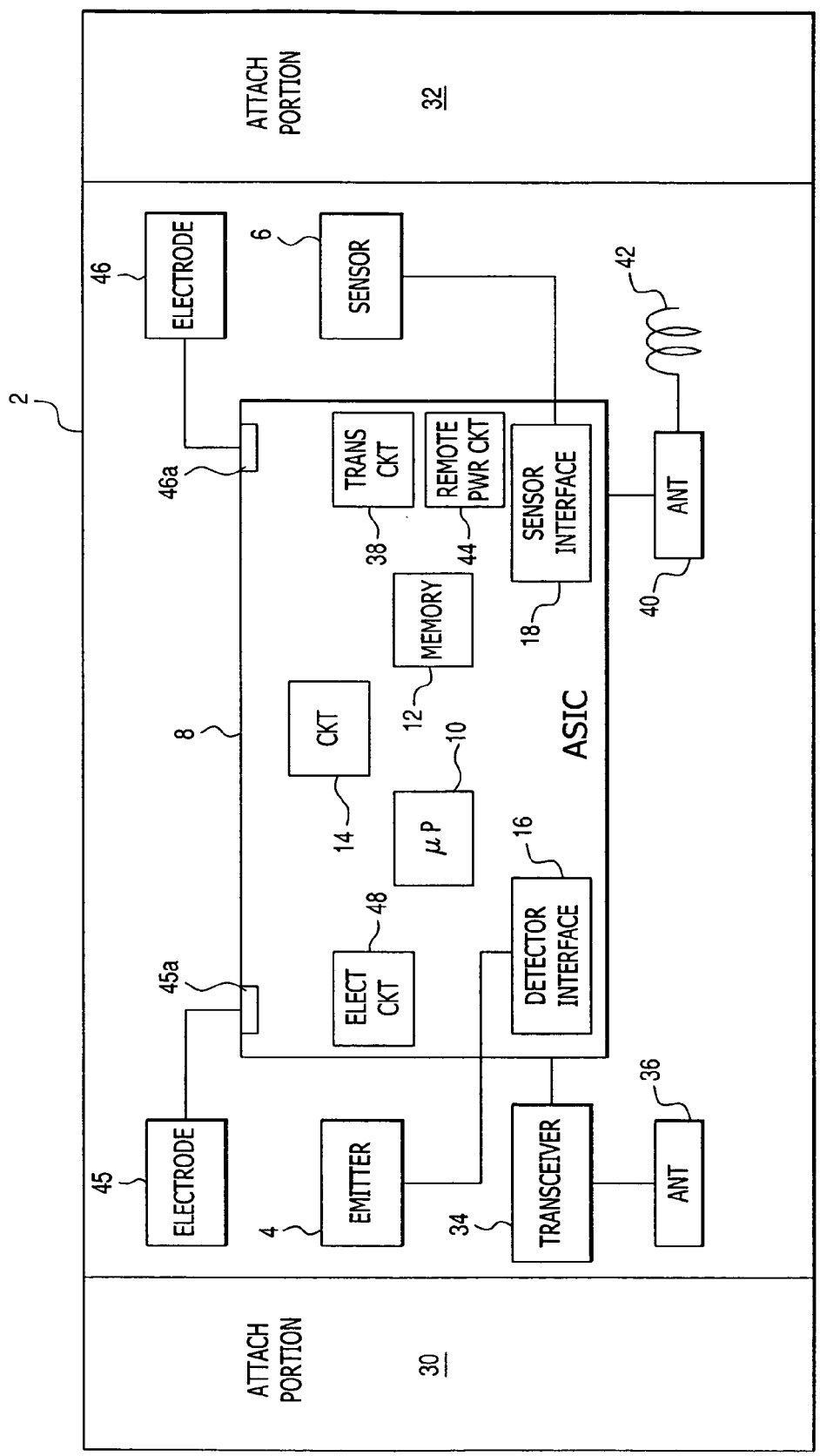
FIG. 10 is a block diagram of the patch oximeter of FIG. 9, but with the display and alarms removed.

FIG. 10 shows the patch oximeter of FIG. 9 but without any display or alarm. Such wireless oximeter/electrode combination patch may be used where there is no need for the patient to view any readings or hear any alarms, as for example in the above-discussed sleep apnea study where the patient is asleep while measurement of the various physiological parameters of the patient takes place.

Figure 11:
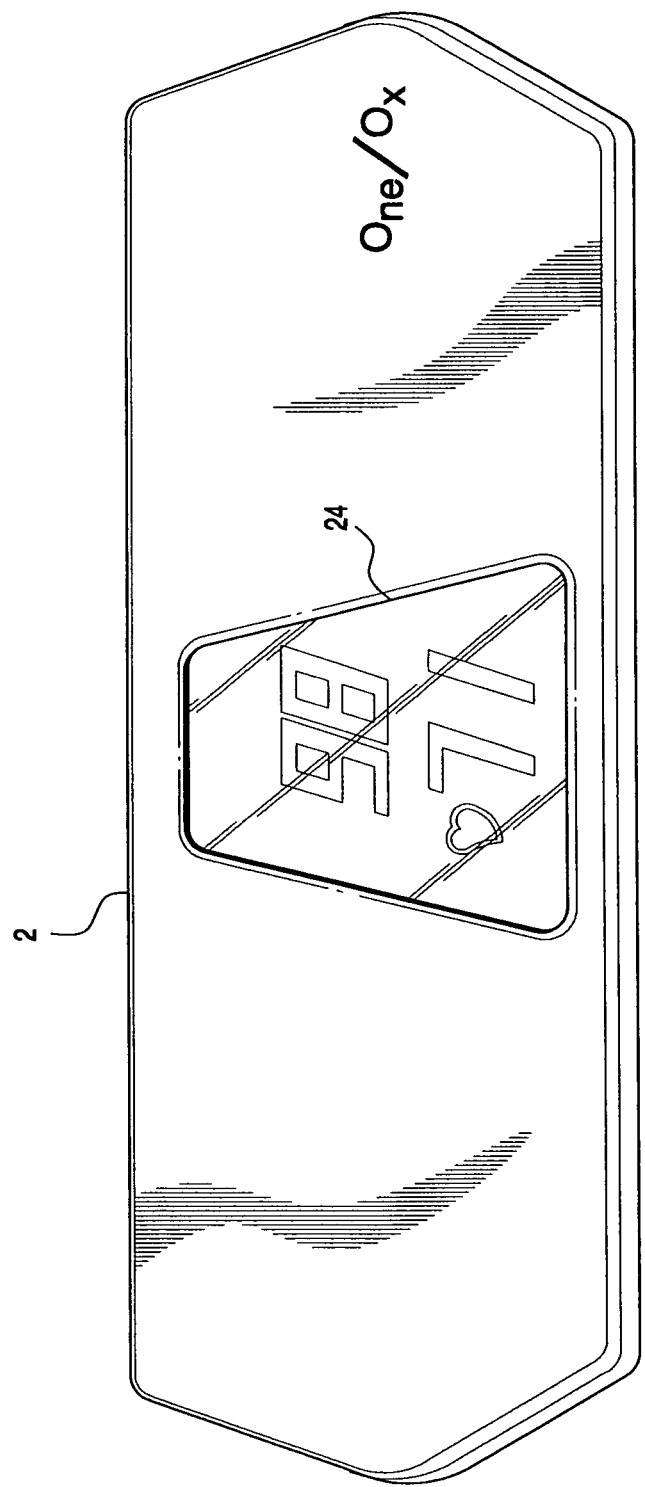
FIG. 11 is an illustrated top view of an exemplar patch oximeter of the instant invention.

FIG. 11 is an illustration of the patch oximeter of the instant invention in the form of a bandage. As shown, display 24 of the bandage shows both the heart rate and the SpO2 of the patient.

Figure 12:
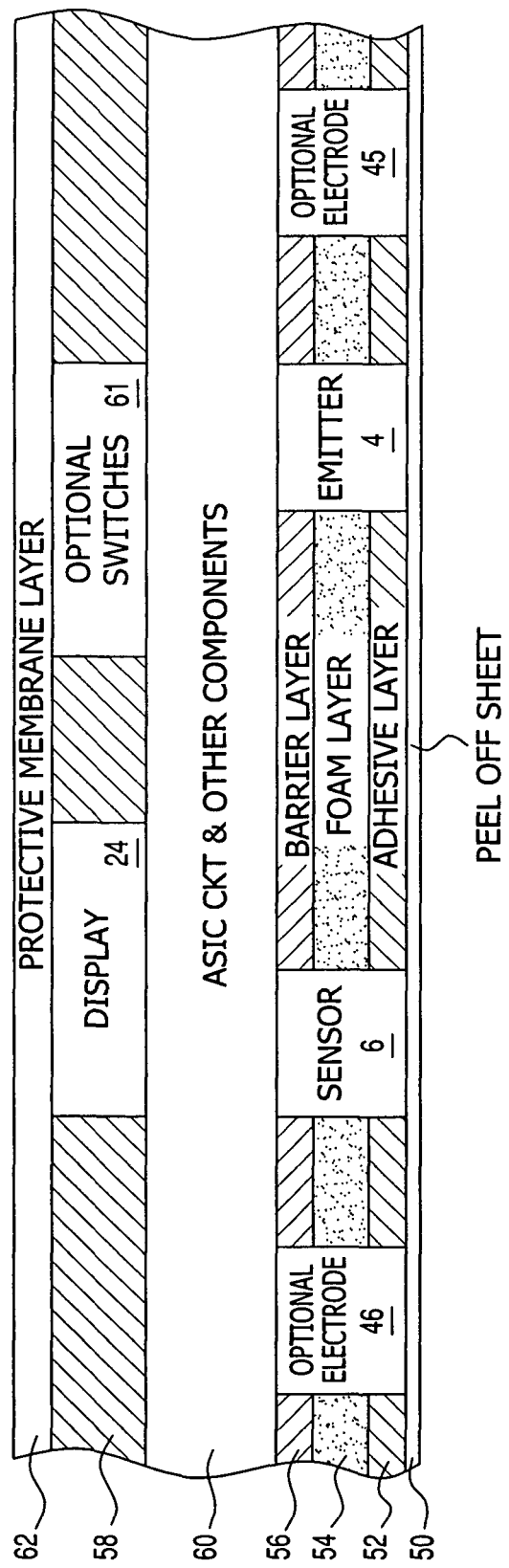
FIG. 12 is a cross-sectional view of the different layers of the patch or bandage strip of the patch oximeter of the instant invention.

FIG. 12 shows in a cross-sectional view the different layers of the patch of the oximeter of the instant invention. It should be appreciate that the various layers shown in FIG. 2 are not drawn to scale or in proportion to their respective thicknesses. As shown, starting with the peel off sheet 50, the layer 52 that comes into contact with the patient is an adhesive layer. As was noted earlier, such adhesive layer may in fact be replaced by appropriate attachment mechanisms such as velcro and snaps. In any event, adhesive layer 52 is prevented from being exposed to the environment by the peel off sheet or paper 50. Above adhesive layer 52 is a foam layer 54 that provides comfort to the patient and also compensates for movements of the patient. On top of foam layer 54 is a barrier layer 56, which may be a plastic sheet or a polyimide sheet that acts as a moisture resistant and electrically insulation layer.

Protected by barrier layer 56 on its lower side and another barrier layer 58 on its upper side is the electronics layer 60 whereby the various electronic components including the ASIC circuit and the other circuits mentioned previously are embedded or mounted. The electrical interconnections among the various components and/or the ASIC circuit with emitter 4 and sensor 6 are represented by the electronics layer 60 being in direct contact therewith. Emitter 4 and sensor 6 each are shown to be extending from electronics layer 60 to be flush with, or slightly above, adhesive layer 52. The optional electrodes 44 and 46 likewise are shown to extend from electronics layer 60 to adhesive layer 52. Although shown as being flush with adhesive layer 52, to operate more efficiently, the surfaces of the electrodes may in fact extend slightly beyond adhesive layer 52 and may be pre-gelled. In any event, each of the contact surfaces of emitter 4, sensor 6 and electrodes 44, 46 are protected by peel off sheet 50.

As noted above, the electronics layer is sandwiched by two protective barrier layers 56 and 58. As shown in FIG. 12, display 24 extends from electronics layer 60 to be flush with the top surface with barrier layer 58. Alternatively, display 24 may be mounted within electronics layer 60, as barrier layer 58, similar to barrier layer 56, may be a clear plastic moisture resistant and electrically insulating sheet that allows the display to be seen from the top of the patch. Also shown are optional switches 61 that may be a part of barrier layer 58 or be embedded in electronics layer 60. Barrier layer 58 is topped with a protective membrane layer 62 that may have graphics printed thereon and appropriate clear window areas, so that display 24 may be viewed, per shown in FIG. 11. With the appropriate graphics printed on protective membrane layer 62, if optional switches 61 are provided, the patient can readily determine which switch to push in order to activate/deactivate the operation of those components to which the caregiver/patient is allowed to control, for example optional display 24 and/or alarm 26, which are not shown in the FIG. 12 patch layers.

Figure 13:
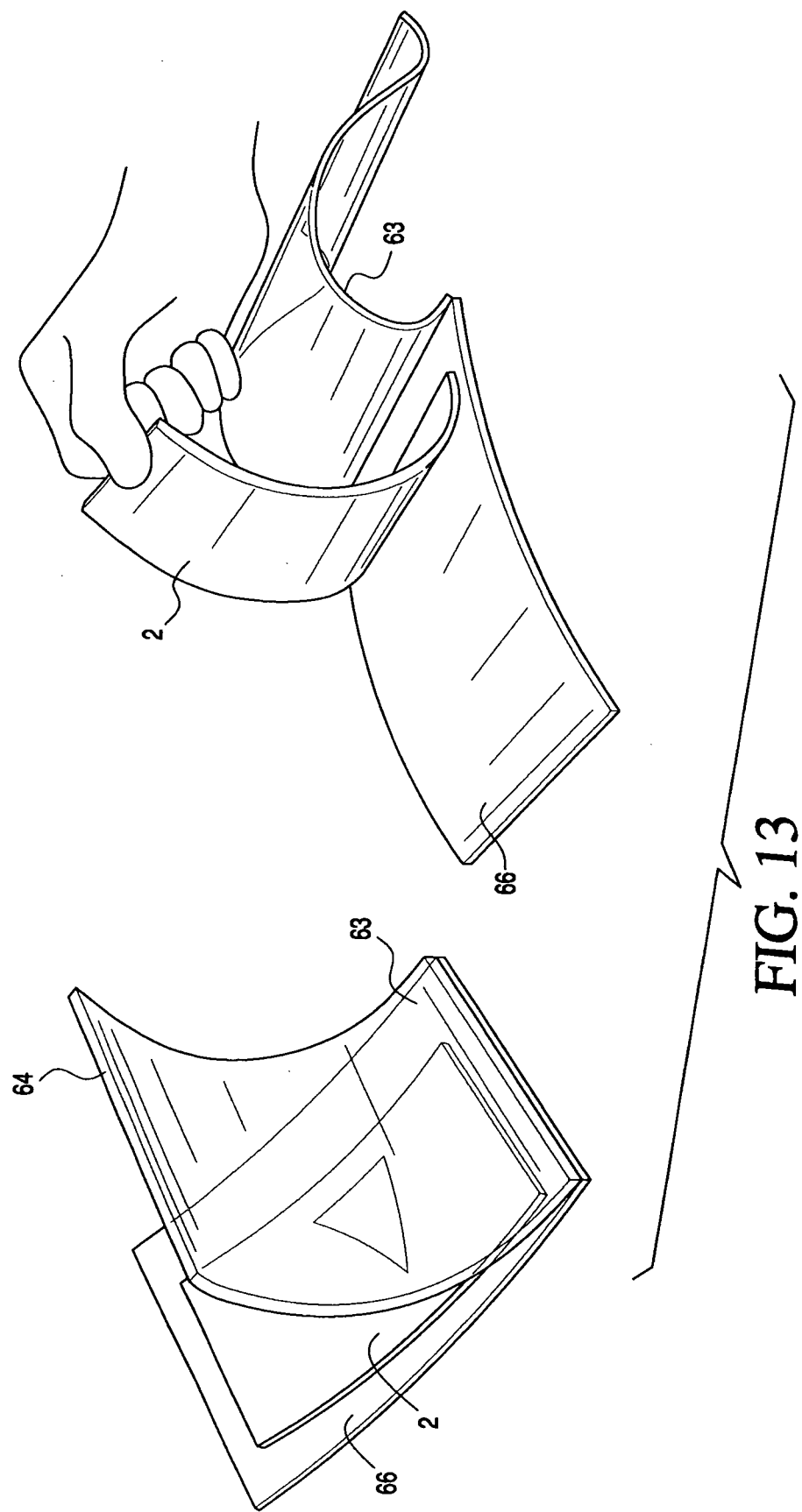
FIG. 13 illustrates an exemplar sterile package of the disposable oximeter of the instant invention, and the removal of the oximeter from the sterile package.

FIG. 13 illustrates the packaging of the patch oximeter of the instant invention. Patch 2 may be housed or stored in a package 63 that includes a clear top wrap 64 and a bottom wrap 66. Bottom wrap 66 may be the peel off sheet 50 shown in FIG. 12 which may have the additional function of activating battery 28 when peeled off, if battery 28 is a fuel cell type battery that utilizes the zinc/air chemistry to operate. Such battery, when stored in air tight environment, is inactive. But as soon as the sheet, for example 50, is peeled off from the patch, the battery becomes activated due to its exposure to air. This feature is advantageous in that it allows the patch oximeter to be stored for an extended length of time. The battery should have sufficient power to operate the oximeter for an appropriate length of time, for example 8-10 hours. Battery 28 may also be a photovoltaic type battery in which power is supplied when the battery is exposed to light. When a photovoltaic battery is used, the placement of the battery on the patch is such that light is allowed to reach the photovoltaic cell via a clear window provided at the membrane layer 62. The peeling off of sheet 50 from the adhesive layer may also be used to activate the above-mentioned chemical light source, which presumably begins its chemical reaction when exposed to air or light.

Figure 14:
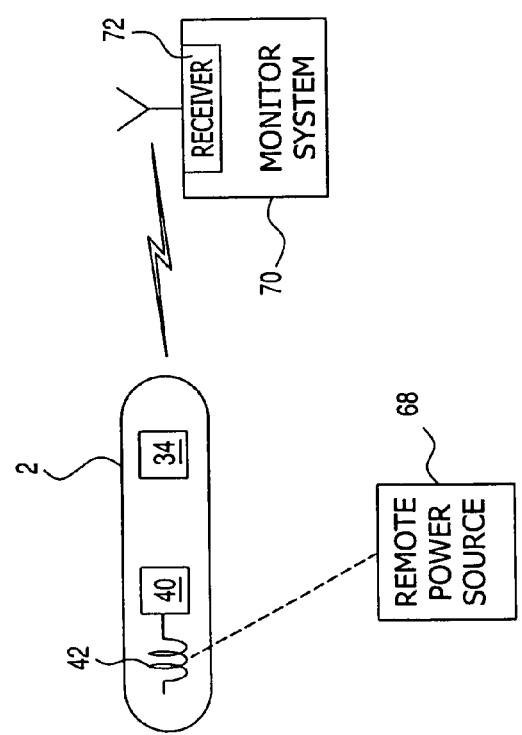
FIG. 14 is a simplified diagram of a patch oximeter of the instant invention communicating with a remote monitoring system.

FIG. 14 illustrates the telecommunication functionalities of the wireless embodiment of the patch oximeter of the instant invention. Patch oximeter 2 retrieves power from a remote power source 68 when it is within a given distance therefrom (for the non-self powered wireless patch oximeter), and then transmits data collected from the patient and/or the calculated SpO2 to the monitor system 70 via the latter's receiver 72. The operation of the transmission of the data from patch oximeter 2 to the monitor system is similar to that given in the above incorporated by reference '962 patent, which discloses the use of an RF link for transmitting data packets from the oximeter to the monitor system 70, and the unpacking of the packets by the monitor system 70.

Figure 15:
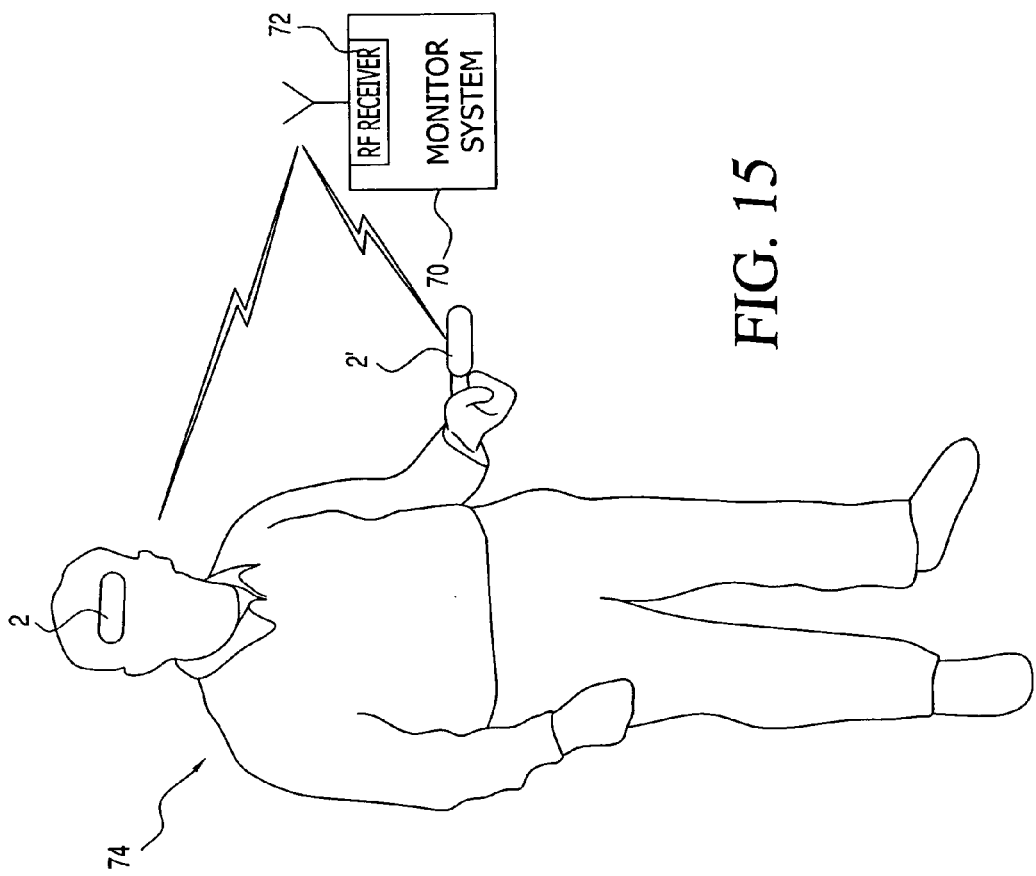
FIG. 15 is a simplified drawing showing a plurality of patch oximeters of the instant invention attached to different areas of a patient to provide a differential measurement of the SpO2 or perfusion of the patient, which may be indicative of whether the patient is in shock, to a remote monitor system.

FIG. 15 illustrates the use of a plurality of patch oximeters of the instant invention, in their wireless form, for transmitting information to a remote device for informing the medical personnel whether the patient is in shock. As shown, a patch oximeter 2 is attached to the forehead of patient 74. Another patch oximeter 2' is attached to an extremity, for example a finger digit of the patient. As each of the patch oximeters measures the SpO2 of the patient at their respective locations, the respective rates of blood perfusion at the forehead and at the extremity of the patient are also measured and the differential between the measurements is determined. This is important insofar as when a person goes into shock, for example hypovolemic shock, the extremities of the patient would tend to shut down the blood perfusion before the brain. Thus, by comparing the difference in the perfusion measurements between an extremity and the forehead of the patient, a determination could be made on whether the patient is about to go into shock, or is in shock due to potential bleeding. With the patch oximeter of the instant invention, if appropriate electrodes which are adaptable to measure the temperature or other physiological parameters of the patient are added, septic or systolic shock may also be measured. As is known, perfusion is conventionally represented by an index, calculated as the ratio of the peak-to-peak red transmission signal to the peak-to-peak infrared transmission signal. See for example U.S. patent publication 2003/0236452, the disclosure of which being incorporated by reference herein.

A flow diagram illustrating the method of determining whether a patient is in shock or at the onset of shock is provided in the flow chart of FIG. 16. Specifically, the process of determining shock in the patient begins with the attachment of a plurality of the patch oximeters of the instant invention to the patient, per step 76. Perfusion measurements are obtained from the oximeter per step 78. A determination is made, per step 80, on whether there is a perfusion differential between the measurements at for instance the forehead and an extremity of the patient. If there is a differential, such differential is compared with a predetermined condition range, for example a predefined 1-10, that has been pre-calibrated to determine whether the patient is okay, at the onset of shock, or already in shock. For the exemplar 1-10 scale, assume that 1-4 correspond to normal, 5-8 correspond to possible onset and 9-10 correspond to the patient being in shock. The comparison of the measured perfusion differential with the predetermined scale takes place in decisional steps 84 and 86. If the measured perfusion differential is within the shock range, then a shock status is sent out per step 88. On the other hand, if the measured differential is within the range that the patient is at the onset of shock, such on the verge status is sent out per step 90. If the patient appears to be stable and not in shock, the process returns to the monitor phase whereby the differences in the measurements between the at least two areas of the patient where the patch oximeters of the instant invention are attached are continuously monitored and calculated. As with the different patch oximeter embodiments of the instant invention, the patch oximeters, once used, are disposed of.

The invention claimed is:

1. A system comprising:
a multi-layer flexible patch adapted to be attached to a patient, at least one light emitter and at least one light detector each integrally mounted to said patch, said one light detector configured to detect the light from said one light emitter passing through or reflected from the patient and acquiring therefrom data relating to at least the oxygen saturation level of blood of the patient, an electronic circuit mounted to an electronics layer of said patch for effecting operation of said one light emitter and said one light detector, a transceiver mounted to said patch to enable said patch to at least transmit a signal representative of the acquired data of the patient, attachment means provided at said patch to enable said patch to be removably attached to the patient, the electronics layer sandwiched between at least two protective layers; and
a remote device in wireless communication with said patch.

2. System of claim 1, wherein said remote device comprises a monitor for receiving the signal from said patch.

3. System of claim 1, wherein said electronic circuit of said patch calculates from the acquired data at least the oxygen saturation level of blood of the patient, the oxygen saturation level of blood being sent as the signal to said remote device.

4. System of claim 1, wherein said patch is adapted to receive information from said remote device.

5. System of claim 1, wherein said remote device comprises an other multi-layer patch having at least one light emitter and at least one light detector each mounted to said other patch, an electronic circuit mounted to an electronics layer of said other patch, and a transceiver mounted to said other patch for communicating with said patch.

6. System of claim 1, further comprising a plurality of other multi-layer patches each having at least one light emitter and at least one light detector mounted thereto, an electronic circuit mounted to an electronics layer of each of said other patches, and a transceiver mounted to each of said other patches for communicating with said patch and others of said other patches.

7. System of claim 1, further comprising a plurality of other multi-layer patches each having at least one light emitter and at least one light detector mounted thereto, an electronic circuit mounted to an electronics layer of each of said other patches, and a transceiver mounted to each of said other patches, wherein said patch and said other patches all transmit information to said remote device.

8. System of claim 1, wherein said patch is adapted to receive power from a remote power source when it is within a given distance from said remote power source.

9. System of claim 1, wherein said patch comprises a power source mounted thereon for supplying power to said electronic circuit, said transceiver and said one light emitter.

10. A system, comprising:
a plurality of multi-layer flexible patches each adapted to be attached to a patient, each of said patches having integrally mounted thereto at least one light emitter and at least one light detector, the one light detector configured to detect the light from the one light emitter passing through or reflected from the patient and acquiring therefrom data relating to at least the oxygen saturation level of blood of the patient, an electronic circuit mounted to an electronics layer sandwiched by at least two protective layers for effecting operation of the one light emitter and the one light detector, a transceiver to enable said each patch to at least transmit a signal representative of the acquired data of the patient, and attachment means to enable said each patch to be removably attached to the patient; and
a remote device in wireless communication with said plurality of patches.

11. System of claim 10, wherein said remote device comprises a monitor for receiving the signals from said plurality of patches.

12. System of claim 10, wherein said plurality of patches each are adapted to receive information from said remote device.

13. System of claim 10, wherein said plurality of patches each are adapted to communicate with at least another one of said plurality of patches.

14. System of claim 10, wherein said plurality of patches each are adapted to retrieve power from a remote power source when said each patch is within a given distance from said remote power source.

15. System of claim 10, wherein said plurality of patches each comprise a power source mounted thereon for supplying power to its electronic circuit, transceiver and at least one light emitter.

16. In combination, a plurality of multi-layer flexible patches and at least one remote device, each of said plurality of patches adapted to be attached to a patient, each of said patches having integrally mounted thereto at least one light emitter and at least one light detector for acquiring data relating to at least the oxygen saturation level of blood of the patient, an electronic circuit mounted to an electronics layer sandwiched by at least two protective layers for at least effecting operation of the one light emitter and the one light detector, a transceiver to at least transmit the acquired data of the patient to said remote device, and attachment means to enable said each patch to be removably attached to the patient.

17. Combination of claim 16, wherein said remote device comprises a monitor for receiving data from said plurality of patches.

18. Combination of claim 16, wherein said plurality of patches each are adapted to communicate with at least another one of said plurality of patches.

19. Combination of claim 16, wherein said plurality of patches each are adapted to retrieve power from a remote power source when said each patch is within a given distance from said remote power source.

20. Combination of claim 16, wherein said plurality of patches each comprise a power source mounted thereon for supplying power to its electronic circuit, transceiver and at least one light emitter.

\* \* \* \* \*